United States Patent [19]

Rich, Jr. et al.

[11] 4,242,097

[45] Dec. 30, 1980

[54] METHOD AND APPARATUS FOR QUANTITATIVE ANALYSIS OF WEAKLY IONIZED ANIONS OR CATIONS

[75] Inventors: William E. Rich, Jr., Mountain View; Edward L. Johnson, Milpitas; Thomas O. Sidebottom, Palo Alto, all of Calif.

[73] Assignee: Dionex Corporation, Sunnyvale, Calif.

[21] Appl. No.: 17,576

[22] Filed: Mar. 5, 1979

[51] Int. Cl.³ .................. G01N 31/04; G01N 31/08
[52] U.S. Cl. .................. 23/230 R; 422/70; 210/656; 210/198.2; 210/662
[58] Field of Search ............ 23/230 R; 422/70; 210/31 C, 198 C, 24, 25, 38

[56] References Cited

U.S. PATENT DOCUMENTS

| | | | |
|---|---|---|---|
| 3,920,397 | 11/1975 | Small et al. | 23/230 R |
| 3,920,398 | 11/1975 | Small et al. | 422/70 X |
| 3,926,559 | 12/1975 | Stevens | 422/70 X |

Primary Examiner—Michael S. Marcus

Attorney, Agent, or Firm—Flehr, Hohbach, Test, Albritton & Herbert

[57] ABSTRACT

Method and apparatus for quantitative analysis of weakly ionized anions (e.g. carboxylates) or cations (e.g., organic amines). For anion analysis, the sample and a strong acid (e.g., HCl) eluent are passed through an ion exclusion chromatography column (cation exchange resin) to resolve the weak anions while eluting the strong anions in the void volume peak. HCl is stripped on an ion exchange stripper column in the silver ion form and the effluent is directed through a conductivity cell and associated readout for detection. For weak cation analysis, the sample and a strong base (e.g., Ba(OH)$_2$) eluent are passed through an ion exclusion chromatography column (anion exchange resin) to resolve the weak cations while eluting the strong cations (e.g., Na$^+$, K$^+$) in the void volume peak. Ba(OH)$_2$ is stripped on an ion exchange stripper column in the sulfate ion form and the effluent is directed through a conductivity cell and associated readout for detection.

25 Claims, 3 Drawing Figures

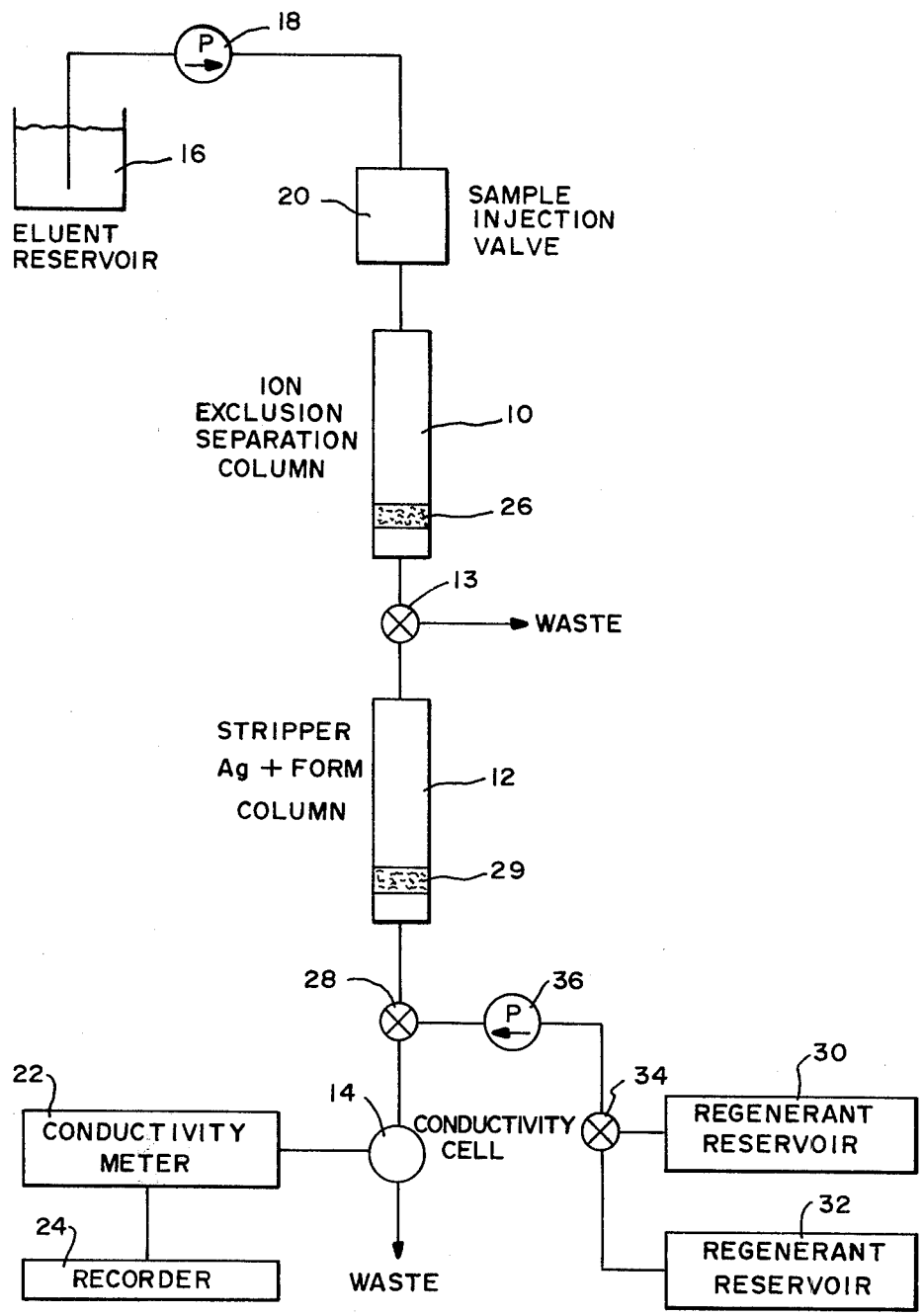
FIG.—1

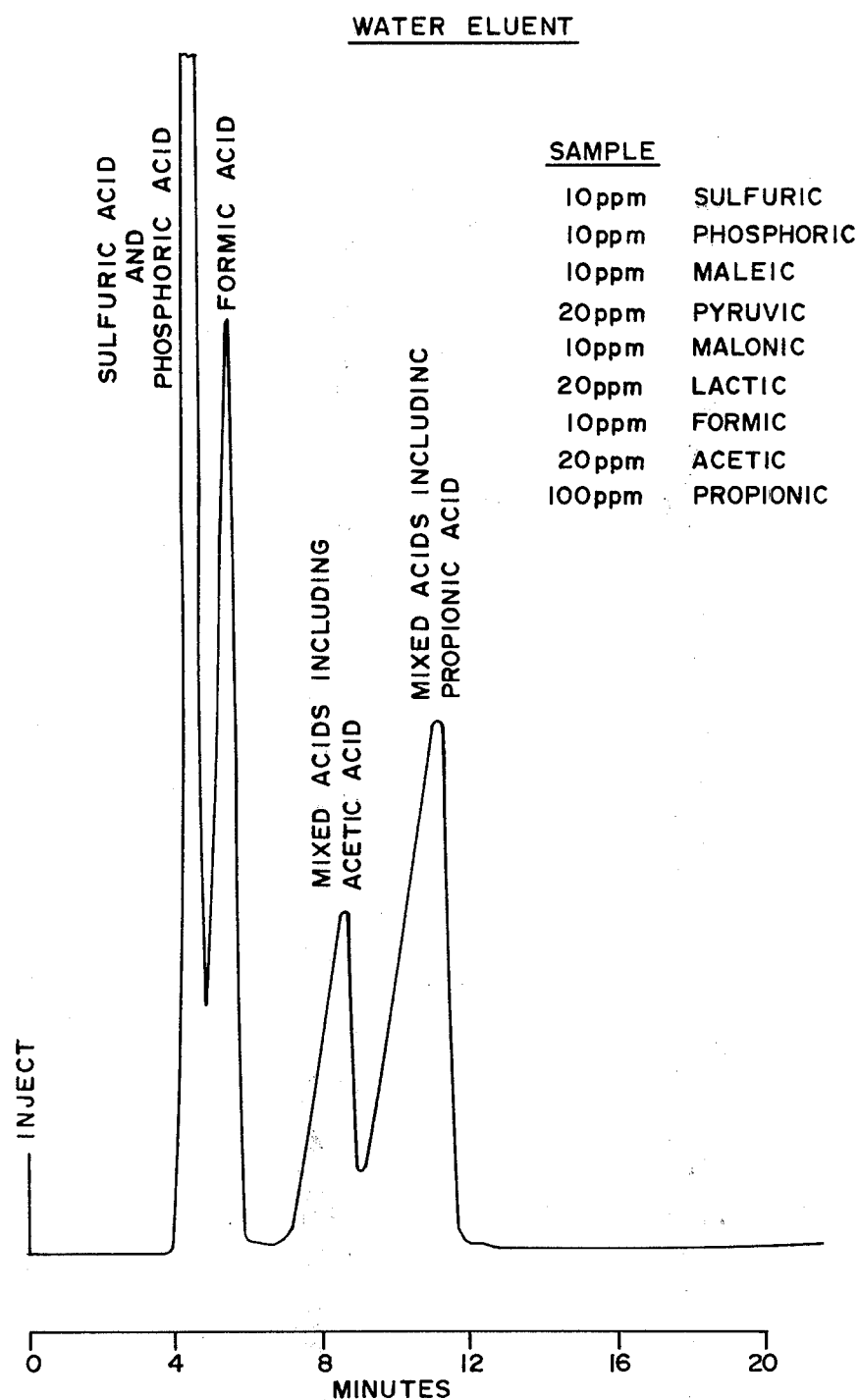
FIG.—2

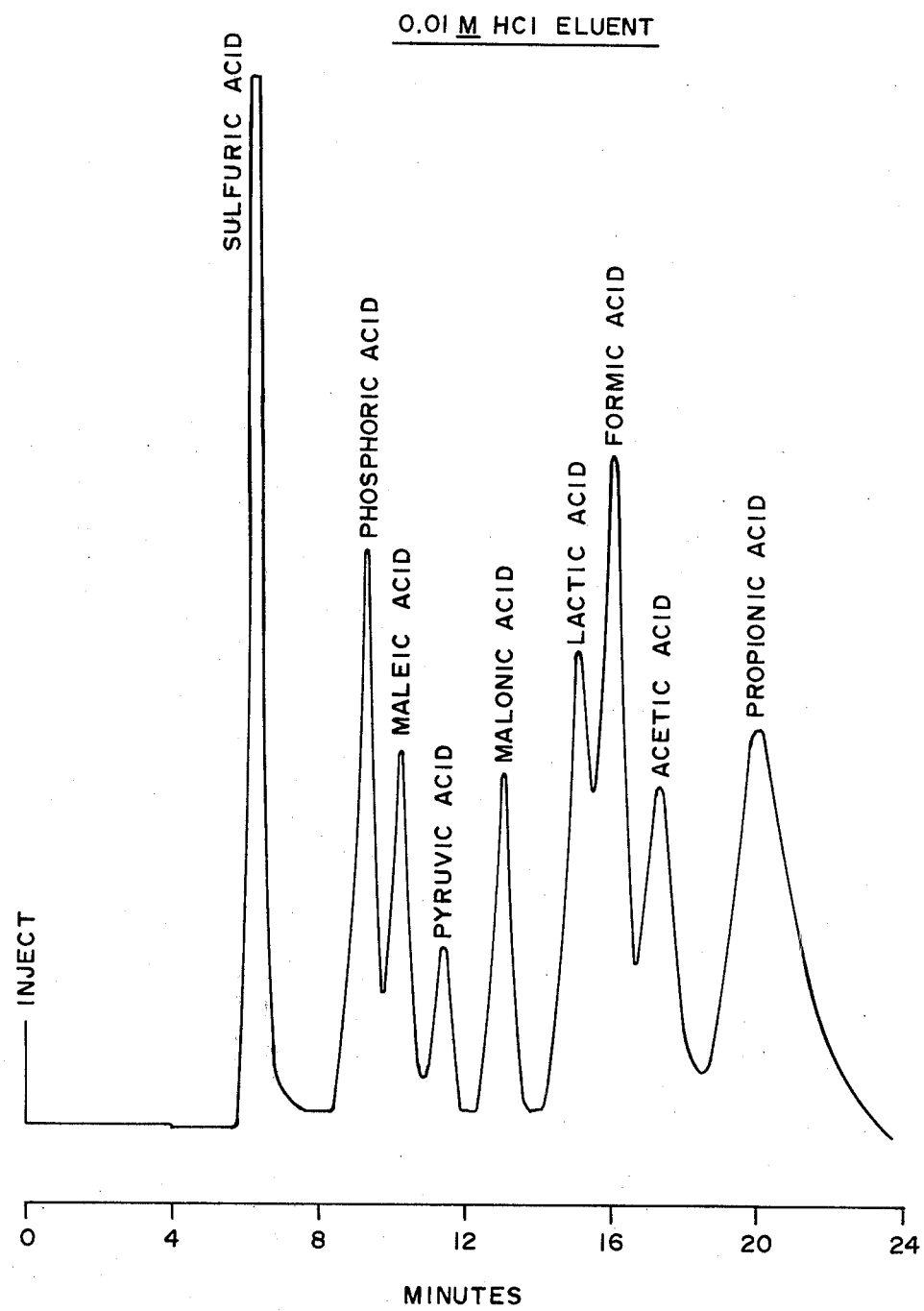
FIG.—3

METHOD AND APPARATUS FOR QUANTITATIVE ANALYSIS OF WEAKLY IONIZED ANIONS OR CATIONS

CROSS-REFERENCE TO RELATED APPLICATION

Reference is made to our copending application entitled "Combination Apparatus and Method for Chromatographic Separation and Quantitative Analysis of Multiple Ionic Species", Ser. No. 017,575, filed simultaneously herewith.

BACKGROUND OF THE INVENTION

The invention relates to method and apparatus for quantitative chromatographic analysis of a mixture of weak anions (e.g., organic carboxylates) or weak cations (e.g., ammonia, organic amines) in aqueous sample solutions.

Heretofore, mixtures of organic carboxylic acids or their carboxylate salts have been analyzed by chromatographic separation with a single column of ion exchange resin followed by detection with an electrical conductivity device. If water soluble metal halides are present in the sample, a pre-column of silver from cation exchange resin is used in addition to the chromatographic column to remove excess halide ions by precipitation. A system of this type is described in Small et al U.S. Pat. 3,920,398. This method allows separation and detection of the carboxylic acids or their salts. The above system is subject to a number of drawbacks. Detection limits range from approximately 0.1 parts by per million (ppm) for acids with one to three carbon atoms, approximately one ppm for acids with four to five carbons and approximately 1 to 100 ppm for acids with 8 to 10 carbon atoms. Also, chromatographic resolution of these low molecular weight carboxylic acids is limited by the necessity of using a very low electrically conducting eluent such as water. This latter requirement is necessary due to the use of an electrical conductivity detector; otherwise, high ionic strength eluents would give rise to high conductivity background and further limit detection sensitivity.

Ion chromatography (IC) has been used to determine both organic carboxylic acids and amines. An IC system for separating cations is described by Stevens U.S. Pat. 3,926,559. IC has the general problem that in anion analysis, weak and strong anions (e.g., organic acids and inorganic anions) coelute unresolved making quantitative analysis of these species difficult. This is also true for weak and strong cations (e.g., organic amines and alkali metal ions). Also, multi-charged weak anions and cations are difficult to elute by IC requiring high eluent concentrations. This necessarily increases the regeneration frequency of the suppressor column and, in a practical sense, measurably adds difficulty to the analysis. Also, because the salt of a weak acid must be used as eluent for IC anion analysis, analysis of that particular weak acid in the sample is precluded.

SUMMARY OF THE INVENTION AND OBJECTS

It has now been discovered that chromatographic quantitative analysis of a plurality of different weak anions (e.g., organic carboxylates) thereof in admixture with any strong mineral acid, or halide or hydroxide of a soluble metal (e.g., alkali) in aqueous solution is readily performed at detection limits substantially less than such prior art techniques and with substantially higher chromatographic resolution. A predetermined amount of the sample solution is added to a first cation exchange resin bed, charged with a cation exchange resin in the hydrogen ion form and eluted therefrom in resolved form with a strong (e.g., mineral) acid such as hydrochloric acid. The acid significantly improves resolution. The effluent is directed to a second cation exchange resin bed charged with a cation exchange resin in a form which will precipitate the mineral acid eluent, e.g., silver ion form for hydrochloric acid eluent, and directing the effluent from the second resin bed means to a conductivity cell having associated readout means. An analogous technique is employed for the separation of cations.

Apparatus used according to the invention for anion analysis includes a strong acid eluent reservoir and an associated pump for directing eluent, through a sample injection valve to a first chromatographic column charged with a cation exchange resin in the hydrogen ion form. This column is connected to a stripper column charged with a cation exchange resin in a form to remove the strong acid. The stripper column is connected to a conductivity cell and associated readout means. Appropriate changes are made for analyzing cations.

Further objects and features of the invention will be apparent from the following description taken in conjunction with the appended drawing.

BRIEF DESCRIPTION OF THE DRAWING

FIG. 1 is a schematic representation of apparatus for carrying out chromatographic separation and quantitative analysis according to the present invention.

FIGS. 2 and 3 are comparative chromatograms illustrating the superior separations obtained by using a strong acid eluent in accordance with the present invention.

DETAILED DESCRIPTION OF THE PREFERRED EMBODIMENTS

The present method and apparatus are well adapted for the rapid and automated analysis of a mixture of weak anions (e.g., organic carboxylates) or weak cations (e.g., ammonia and organic amines) both being in aqueous solution containing up to the saturation limits of soluble metal halide and/or soluble strong (highly dissociated) metal hydroxide and/or strong (highly dissociated) acid. The determinable weak anions or cations include any of such compounds soluble enough to be present in the sample solution at a concentration at least equal to the detection limit of the conductivity cell, usually below about 20 parts per billion (ppb) of carboxylic acid or salt and below about 100 ppb of ammonia or amine.

As defined herein, "weak anions" are anions which, are poorly ionized in acid form, and which are resolved by ion exclusion chromatography in comparison to "strong anions" which are defined to be highly ionized in acid form, have a relatively low $pK_A$ value (e.g., 0 to about 2) and which are not resolved by ion exclusion chromatography. Strong and weak acids are defined to be acids of strong and weak anions, respectively.

As further defined herein, "weak cations" are cations which are poorly ionized in base form, and which are resolved by ion exclusion chromatography in comparison to "strong cations" which are defined to be highly ionized in base form, have a relatively high $pK_B$ value (e.g., about 0 to 2), and which are not resolved by ion exclusion chromatography. Strong and weak bases are defined to be bases of strong and weak cations, respectively.

Typical weak anions include mono- carboxylate groups (e.g., formate and acetates), di- and tri-carboxylate groups, nitrite, alkyl sulfates, carbonate, alkyl sulfonate and their hydroxy and halogenated derivatives. Typical strong anions includes strong mineral acids and specifically include halide, sulfate, chlorate, nitrate, sulfite, and chromate. Typical weak cations include ammonia, primary, secondary and tertiary alkyl organic amines with less than 20 carbon atoms and alkyl di-amines, triamines and some quarternary amines. Typical strong cations include alkali and alkaline earth metals.

Referring to weak anion analysis, the method is of particular advantage for the analysis of non-aromatic carboxylic acids and their carboxylate salts, including the mono-carboxylic fatty acids having from 1 to about 10 carbon atoms in the molecule and the di- and tri-carboxylic acids having up to about 10 carbon atoms in the molecular as well as the corresponding hydroxy and halide substituted acids. Beyond 10 carbon atoms, the advantages of the present system are not as apparent. Other weak anion compounds including non-aromatic acids such as alkyl sulfonic acid and phosphonic acids can also be determined by this method if they have approximately 10 or less carbon atoms and their silver salt forms are soluble. Although the system could also be used to analyze aromatic acids, they are readily analyzed by U.V. detectors.

Referring to the weak cation analysis, the method is of particular advantage for the analysis of organic alkyl primary, secondary and tertiary amines, alkanol amines, ammonia, polyamines and their corresponding hydroxy and halide substituted derivative having about 20 carbon atoms in the molecule.

For simplicity of description, the specification will first refer to weak anion analysis, specifically of the carboxylic acids or their salts. They readily separate from soluble metal halides or hydrohalides as well as from each other which heretofore has represented an analytical problem preventing easy, rapid, low cost analysis. Analysis of such weak anions is carried out by the present method on passing the sample solution through a cation exchange resin in the hydrogen ion form whereby the carboxylic acids are separated chromatographically. The strong, highly dissociated mineral acids or their salts are completely converted to the acid form by ion exchange action, pass directly through the column in the void volume unretained while the weaker, less dissociated carboxylic acids or their salts are first completely converted to the acid form by ion exchange action, then due to suppression of ionization caused by the strongly acidic eluent, are absorbed by the ion exchange resin and chromatographically separated.

In general, the sample is eluted through a chromatographic column of the "ion exclusion" type using an eluent with a strong acid developing reagent. The theory of the technique is that the resin network serves as a boundary, which behaves as a semipermeable membrane, between the interstitial liquid between the resin particles and the occluded liquid inside the resin. Due to Donnan exclusion, highly ionized molecules, such as strong mineral acids, are excluded from the resin particles and passed directly through the column in the void volume peak. Weak anion molecules, such as many carboxylic or other organic acids and their salts (e.g., acetate and formate), may enter the resin phase in acid form and are retained by the resin for later elution than strong acids. Weak acids and their salts are readily separated from strong acids and their salts. The sample is passed over the column preferably charged with a cation exchange resin in the hydrogen ion form using an aqueous solution of a strong acid as the eluent. In special applications, non-aqueous solvents such as alcohol and acetonitrile may also be used as the eluent. Salts of weak acids are converted in the presence of the strong acid to their free acid form, and the cation of metal hydroxide in the sample are neutralized by ion exchange action. Separation of the weak acids from the strong acids or their salts occurs as the sample moves through the resin bed in accordance with the foregoing principles.

Chromatographic separation by ion exclusion is principally due to the distribution coefficient $K_d$, which equals $C_r/C$. $C_r$ is the concentration of the solute in the liquid phase inside the resin and C is the concentration of solute in the liquid phase outside the resin particles. Separation depends upon factors which effect $K_d$ such as $pK_A$, concentration of the solute and characteristics of the resins such as cross-linkage and ion exchange functionality. Generally, the $pK_A$ can be used to predict elution order but van der Waals forces can become dominant if the number of aliphatic or aromatic carbons become large as with fatty acids. Altering the pH level of the eluent has a pronounced effect upon the separation of weak acids because the degree of ionization changes with pH.

In general, the weak acids in their molecular unionized form can penetrate into the interior of the ion exchanbe resin while the strong highly ionized acids are excluded. By using ion exchange resin in hydrogen ion form, salts of weak acids which are highly ionized (e.g., of alkali metals) are converted to their acid form which are temporarily retained and resolved on the column and eluted while the cation is firmly retained. For example, sodium acetate is converted on the column to acetic acid and the sodium is retained by the column. Thereafter, the acetic acid is resolved from other weak acids and eluted from the column in a separate peak volume which can be detected. The above discussion of ion exclusion chromatography applies in an analogous manner to the separation of cations. However, in this case, an anion exchange resin is employed.

The resin employed in the ion exclusion column is of a type in which the dominant retentive force is penetration of the weak acid in molecular form into the interior of the resin for retention there for a time until elution in the eluent stream in inverse order to such retention forces. This effect is additive to any ion exchange effect. To permit this to occur, the pore size of the resin should be relatively large to permit rapid diffusion of such molecules. A suitable substrate of this type is a microporous sulfonated copolymer of styrene and divinylbenzene having about 1 to 8% divinylbenzene cross-linking. Suitable ion exchange groups for anion analysis include sulfonic acid type and for cation analysis include trimethylammonium or dimethylethanolammonium type. Suitable sizes for the particles are on the order of 200 to 400 mesh (U.S. sieve series) although finer sizes may be used if desired. The specific exchange capacity of the resin particles is not critical. A suitable level is on the order of about 0.5 to 5 milliequivalent per gram (m.eq./g.) of resin. Macroporous polystyrene resins with sulfonic acid or quarternary amine ion exchange sites are also suitable as ion exclusion resins. In this case, the divinylbenzene should be 25% to 100% of the styrene polymer by weight.

Referring to the strong acid developing reagent in the eluent, it should have molarity sufficient to substantially suppress the ionization of all of the sample weak anions to be resolved. This permits the anions in unionized form to penetrate the resin for resolution. Typically, for HCl, a molarity of 0.001 M to 0.05 M is sufficient.

For weak cation analysis, the eluent should contain a strong base developing reagent at a pH basic enough to substantially suppress the ionization of all the sample weak cations present. For example, a molarity of 0.005 M barium hydroxide is usually sufficient. The strong base eluents permit the ions to penetrate into the resin in the undissociated form, enhancing chromatographic resolution.

In weak anion analysis, the effluent from the ion exclusion column is directed to the stripper column including a cation exchange resin bed, in the silver ion form if HCl is used as eluent. The HCl eluent is removed by precipitation of silver chloride along with any metal halides by ion exchange action followed by silver halide precipitation. The effluent, consisting mainly of weak acids (e.g., carboxylic acids), silver soluble salts, and water, elutes into the conductivity cell where detection of the silver-soluble salts and carboxylic acids occurs in a low conductivity background of water containing a residual concentration of unprecipitated HCl.

In weak cation analysis, the effluent from the ion exclusion column is directed to the stripper column including an anion exchange resin bed, in the sulfate form, if barium hydroxide is used as eluent. The barium hydroxide in the eluent is removed by precipitation of barium sulfate and hydroxide by ion exchange action. The effluent, now containing weak cations (e.g., organic amines, sulfate soluble salts) elute from the column and into a conductivity cell and are detected in a low conductivity background of water containing a residual concentration of unprecipitated $Ba(OH)_2$.

To summarize, a significant feature of the invention is the use of a strong acid (or strong base) as a developing agent for separation of weak anions (or weak cations) to improve their resolution. However, the high concentrations of developing reagent would interfere with conductivity measurement. This problem is obviated by use of the stripper column.

The mechanics of separation of the carboxylic acids and carboxylate salts or amines on the ion exclusion column as used herein are known and can be manipulated to obtain specific separation of column geometry, the flow rate of the eluent, the nature of the resin used, especially the degree of cross-linking and sulfonation thereof, and in particular, the pH of the eluent.

All carboxylic acids in the sample must be in the ionized form when eluting into the detector to ensure maximum reproducibility. Thus, it is preferable to use the strong acid eluent in combination with ion exclusion resin in the hydrogen form so that all carboxylates in the sample are uniformly in the hydrogen form. In special circumstances, this may be further assisted by adding a small column of cation exchange resin in the hydrogen or sodium form after the stripper column and before the conductivity cell. This converts the soluble silver salts of the weak anions to acids or sodium salts to increase their conductivity and thus detectability. The volume of this column resin bed should be equal to approximately 10–20% of the volume of the stripper column resin bed.

For HCl eluent, the cation exchange resin in the stripper column is preferably. in the silver form, typically polystyrene or modified polystyrene copolymer cross-linked, e.g., with divinylbenzene, and carrying functional groups, the latter providing the active exchange sites. The strong cation exchange resins carry sulfonic acid or sulfonate functional groups along the polymer chain. Divinylbenzene crosslinkage should be greater than 12% to minimize absorption effects.

Referring now to FIG. 1, the apparatus of the present inventon is seen basically to consist of an ion exclusion chromatographic column 10, a stripper column 12, and an intermediate valve 13, a conductivity cell 14, and liquid conduit means connecting these parts in series. As an example, consider weak anion analysis. Hydrochloric acid eluent is drawn from eluent reservoir 16 by a pump 18 and supplied to column 10 via a sample injection valve 20. Conductivity cell 14 is provided with readout means consisting of a conductivity meter 22 and a recorder 24, the latter preferably being a recorder-integrator.

The system may include means for regenerating the resin in stripper column 12 including regenerant reservoirs 30 and 32 connected by suitable valving 34 to pump 36 and then to valve 28.

Chromatographic column 10 is charged with a cation exchange resin 26 in the hydrogen ion form. Resin 26 may be most any commercially available cation exchange resin but is preferably a high specific capacity resin, homogeneously sulfonated throughout the beads therefore and formed of a copolymer of styrene and divinylbenzene. Suitably, the degree of ion exchange capacity (e.g., sulfonation) is 10–100%, preferably 50–100% of theoretical completeness. The degree of cross-linking is preferably between 1 and 8% dinvinylbenzene in the copolymer.

Stripper column 12 is charged with a cation exchange resin 29 in the silver ion form if HCl is used as eluent or barium ion if sulfuric acid is used as eluent. In the latter case, a separate silver form resin must be used if metal halides are to be removed from the sample in addition to separation of the carboxylic acids. Cation exchange resin 29 is preferably a high specific capacity cation exchange resin and may be one of the generally available commercially sold, e.g., polystyrene or modified polystyrene copolymers cross-linked, with divinylbenzene and carrying functional groups, the latter providing the active exchange sites in the form of sulfonic acid or sulfonate groups along the polymer chain. The cross-linkage of said resin should be 12% to 16% to prevent excessive chromatography based broadening on carboxylic acids in the stripper column.

In carrying out analysis of a mixture of carboxylic acids or carboxylate salts according to the present method, the aqueous sample solution is directed into the chromatographic column 10 by any suitable means as by pipetting or otherwise placing a measured amount of solution on the column but preferably sample is added to the column by injecting a measured amount by means of the sample injection valve 20. The sample injection valve 20 is ordinarily one of the commercially available sample injection valves having a valve plug bore or a loop of tubing connecting to the valve body parts utilized to determine sample size which is subsequently swept out by the eluent as well understood in the art. While the chromatographic separation can be carried out by manually adding eluent hydrochloric acid to the top of the open column, it is much preferred for the purposes of obtaining rapid, highly reproducible results that the eluent be added as a steady stream by the use of a pump such as pump 18.

The carboxylic acids present in the sample solution entering the column 10 are chromatographically separated and generally exit from the column 10 in well defined concentration peaks. Carboxylate ions, if present in the sample, are converted to the unionized form by ion exchange action and are chromatographically separated on column 10. Also, metal hydroxide, is neutralized to water by ion exchange action. Thus, the effluent from the first chromatographic column 10 passes through valve 13 to stripper column 12 free of metal hydroxide if originally present in the sample.

In passing over the stripper column 12, the effluent is stripped of its halide ions by precipitation of silver halide. Strong mineral acids except for hydrohalides and carboxylic acids elute through with little or no further chromatographic separation. The concentration peaks of the carboxylic acid existing from stripper column 12 are empirically detected by the conductivity cell 14. Concentration measurements are achieved by running known standards. The relationship between concentration of carboxylate ion and conductivity cell response has been found to be substantially linear over a large concentration range from very dilute to up to about 0.5 molar carboxylic acid.

Using the preferred resins specified herein or an equivalent performing resin, sharp concentration peaks are obtained and conductivity cells having high sensitivity for the carboxylic acids, the lower molecular weight carboxylic acids such as acetic and formic acids are detectable at concentration levels as low as about 2 parts per billion (ppb). Carboxylic acids such as butyric acid and propionic acid are detectable at concentrations as low as about 5 ppb while carboxylic acids having about 8 to 10 carbon atoms in the molecular are detectable at minimum concentrations in the range of about 1 to 10 parts per million (ppm).

Sample portions added to the column by typical sample injection valve generally run in the range of about 0.002 to 5 milliliters of dilute solution of carboxylic acids which in total are present in an amount commonly expressed in milliequivalents no greater than about 1 to 10% of the ion exchange capacity of the separator bed, thus providing for good resolution on the column. Flow rates of hydrochloric acid for elution generally run in the range from about 0.25 to 2 ml/min. wherein the chromatographic column utilized has a diameter in the range of about 2 to 12 millimeters internal diameter (I.D.).

Referring to FIG. 1, the stripper column resin 24 in the silver form requires periodic regeneration. Regeneration may be carried out by washing the resin sequentially with solutions of ammonium hydroxide and silver nitrate. With the former solution in reservoir 30, valve 34 is actuated and ammonium hydroxide is drawn by pump 36 to valve 28 and upwardly through stripper column 12, through valve 13 and is passed to waste. Then, valve 34 is switched and silver nitrate from reservoir 32 is drawn by pump 36 through valve 28, upwardly through stripper column 12 and valve 13 to waste. After completion of stripping, the system is returned to an operational mode. It is more preferred, however, to remove the exhausted resin and replace it with fresh resin in the silver ion form.

The geometry of stripper column 12 determines the frequency of regeneration for a given eluent concentration as well as loss of chromatographic resolution due to band broadening. Preferably, the stripper column 12 should not exceed the column volume of the ion exclusion separation column 10 and should be at a minimum of 3×250 millimeters. A 3×250 mm column will usually require regeneration every 8 hours, using a 0.01M hydrochloric acid eluent; proportionately less frequently if lower concentrations of eluent can be used.

Although the above system has been described with respect to anion analysis, it is also applicable to cation analysis. A suitable developing reagent is barium hydroxide with the resin in the ion exclusion chromatographic column preferably in hydroxyl form. Barium hydroxide may be stripped with anion exchange resin in the stripper column in the sulfate ion form.

The weak anions or cations to be measured must be significantly ionized at the conductivity cell for measurement by a conductivity meter. For this purpose, the $pK_A$ value for the anion or cation during measurement must be below about 7.0.

Some weak anions (or cations) with corresponding acids (or bases) above this value may be rendered detectable by the conductivity meter by combining with the counterion of the stripper column. For example, HCN has a $pK_A$ value of about 9 and so is undetectable in acid form by a conductivity meter. However, it would complex with silver ion, if silver is used as the stripper column counterion, to form $Ag(CN)_2^-$ with a $pK_A$ value substantially below 7. This complex is readily quantitatively detectable by a conductivity meter. Thus, cyanide is quantitatively analyzable according to the invention. Analogous anions and cations are also analyzable.

The preferred form of the ion exclusion resin is hydrogen for anion analysis and hydroxyl for cation analysis. However, in special applications where the strong acid is in sufficient molarity to suppress all weak anions in the sample, a non-ionic resin may be used. Suitable non-ionic resin includes silica-based so-called "reverse phase" resins (e.g., μBondapak C-18 commercially available from Waters Associates).

A further disclosure of the nature of the present invention is provided by the following specific examples of the practice of the invention. It should be understood that the data disclosed serve only as examples and are not intended to limit the scope of the invention.

EXAMPLE 1

SEPARATION OF ORGANIC CARBOXYLIC ACIDS

A mixture of seven organic acids (malic, pyruvic, malonic, lactic, formic, acetic, and propionic) and two inorganic acids (sulfuric and phosphoric) was injected onto a 9 mm×250 mm bed of 4% cross-linked cation exchange resin in the H+ form. The eluent used was deionized water at a flow rate of 0.86 ml/min. No suppressor column was used. The resultant chromatogram is shown in FIG. 2. Using these conditions, only formate, acetate and propionate can be quantitatively determined.

EXAMPLE 2

The eluent was then changed to 0.01 M HCl. It was found that a stripper column was necessary since the high eluent conductance precluded detection of the solutes. The stripper column employed was a 3×250 mm bed of 16% cross-linked cation exchange resin in the silver form and followed by a 3×250 mm bed of 16% cross-linked cation exchange resin, the first ⅔ of the bed in the silver form and the final ⅓ (prior to conductivity detector) in the H+ form was installed following the 9×250 mm column described above. FIG. 3 shows the results obtained with the acid mixture described in Example 1. There is excellent resolution of all 9 components permitting excellent quantitation.

EXAMPLE 3

The detection limits for acetic and butyric acid were estimated by preparing known stock solutions of the respective acids. A 1 ml loop was used to introduce the sample onto the 9 mm × 250 mm bed of 4% cross-linked cation exchange resin in the hydrogen ion form. The eluent was 0.01 M HCl and the chloride ion was stripped from the eluent using a silver stripper column described in Example 1. The flow rate was 0.86 ml/min.

The calculation of minimum detection limit (MDL) was made using the criteria that 2 times the detector noise was the lowest level detectable. Using 1 $\mu$mho sensitivity the noise was approximately 0.01 $\mu$mho. A 1 ml injection of 0.1 ppm acetic acid yields a signal of 0.65 $\mu$mho and an estimated MDL of 0.002 ppm. For butyric acid, a 1 ml injection of 0.1 ppm yielded a signal of 0.9 $\mu$mho and the resultant MDL of approximately 0.005 ppm.

EXAMPLE 4

In this experiment, trace levels of ammonia in brine was determined. 20 $\mu$l of a solution containing 10 ppm $NH_4^+$ and 2.5% NaCl were injected onto a 9×250 mm column of 4% cross-linked anion exchange resin (20±2 $\mu$m diameter) in the hydroxide ion form. Solutes were eluted by a pumped stream of 5 mM $Ba(OH)_2$ flowing at 0.8 ml/min. The effluent was directed to a stripper column packed with Dowex-1×10 (200–400 mesh) in the sulfate ion form. The effluent from this second column was directed to a conductivity flow cell and detector. Baseline resolution between sodium and ammonium ion was afforded by this method.

EXAMPLE 5

Example 4 was repeated using a pumped stream of water at 0.8 ml/min and omitting the stripper column. Sodium and ammonium ion are incompletely resolved using this system. Ion exclusion using water is inadequate for this separation.

EXAMPLE 6

A mixture of 50 ppm each of ammonia, methylamine, and ethylamine was injected into the system as described in Example 4 above. 20 microliters of the solute were eluted in this case by a pumped stream of an aqueous solution of 5 mM Ba $(OH)_2$, 10% (v/v) acetone flowing at 0.5 ml/min. This method afforded nearly baseline resolution between methylamine and ethylamine, and baseline resolution between these amines and ammonia. Minimum detection limits for the amines under these conditions is about 100 ppb.

EXAMPLE 7

(Comparative—Ion Chromatography)

100 $\mu$l of the material of Example 4 was injected into a 9×250 mm column of a pellicular sulfonated styrene divinylbenzene (DVB) resin used for ion chromatography. Elution was accomplished by a pumped stream of 5 mM $HNO_3$ flowing at 1.5 ml/min. The effluent from this column was directed to a 9×250 mm column of Dowex-1×10 in the hydroxide form (the suppressor column for conventional ion chromatography). The effluent from this column was then directed to a conductivity flow cell and detector. No resolution between these species was seen. Ion chromatography is inadequate for this separation.

EXAMPLE 8

20 $\mu$l of a solution containing 50 ppm each ethylenediamine and ammonia were injected into the system described in Example 4. Baseline resolution between the two components was achieved.

EXAMPLE 9

(Comparative—Ion Chromatography)

100 $\mu$l of the solution of Example 8 was injected into the system described in Example 7. Ethylenediamine was never eluted from the column showing ion chromatography is inadequate for this separation.

What is claimed is:

1. The method of chromatographic separation and quantitative analysis of a plurality of different weak anions of weakly dissociated acids or of salts of weakly dissociated acids, said method comprising
    (a) directing a sample comprising a plurality of different weak anions of weakly dissociated acids or of salts of weakly dissociated acids, in an eluent solution through a chromatographic resin bed, said eluent comprising a strong acid substantially more dissociated than the acids of the weak anions, said strong acid being present at a concentration to substantially suppress ionization of said weak anions, said chromatographic resin being in a form to substantially resolve said weak anions,
    (b) directing the effluent containing said resolved weak anions and said strong acid from step (a) through a stripper column including a cation exchange resin in a form to remove the strong acid anion but not to disturb the resolution of the weak anions from the sample solution, and
    (c) directing the effluent from step (b) containing said resolved weak anions through a conductivity cell having associated readout means.

2. The method of claim 1 in which said strong acid is a hydrogen halide acid, said cation exchange resin is in the silver form, and the halide anion of said acid is removed by precipitation with the silver at its ion exchange site.

3. The method of claim 1 in which said weak anions are derived from acids selected from the group consisting of substituted and unsubstituted non-aromatic carboxylic acids, alkyl sulfonic acids, alkyl sulfuric acids, phosphonic acids, nitrous acid, carbonic acid, and hydrocyanic acid.

4. The method of claim 1 in which said carboxylic acids are selected from the group consisting of unsubstituted mono-, di- and tricarboxylic acids of about 1 to 10 carbon atoms, and the same acids substituted with hydroxy and halide groups.

5. The method of claim 1 in which said chromatographic resin is of the ion exclusion type capable of chromatographically separating said weak anions by selective temporary retention but which passes strong anions in the column void volume.

6. The method of claim 1 in which the chromatographic resin is a cation exchange resin in the hydrogen ion form with ion exchange capacity between 10% and 100% of total theoretical capacity.

7. The method of claim 1 in which said sample includes soluble ionized cations which are removed by ion exchange action with said chromatographic resin.

8. The method of claim 1 in which the chromatographic resin is of a non-ionic type.

9. The method of claim 1 in which between steps (b) and (c) said eluent is directed through a column of ion exchange resin in the hydrogen ion or sodium ion form to convert any soluble silver salts of the weak anions therein to acid or sodium salt form, respectively.

10. The method of chromatographic separation and quantitative analysis of a plurality of different weak cations of weakly dissociated bases or of salts of weakly dissociated bases, said method comprising
 (a) directing a sample comprising a plurality of different weak cations of weakly dissociated bases or of salts of weakly dissociated bases, in an eluent solution through a chromatographic resin bed, said eluent comprising a strong base substantially more dissociated than the bases of said weak cations, said strong base being present at a concentration to suppress ionization of said weak cations, said chromatographic resin being in a form to substantially resolve said weak cations,
 (b) directing the effluent containing resolved weak cations and said strong base from step (a) through a stripper column including an anion exchange resin in a form to remove the strong base cation but not to disturb the resolution of the weak cations from the sample solution, and
 (c) directing the effluent from step (b) containing said resolved weak cations through a conductivity cell having associated readout means.

11. The method of claim 10 in which said strong base is barium hydroxide, said ion exchange resin is in the sulfate form and the barium cation of said base is removed by precipitation with the sulfate at its exchange site.

12. The method of claim 10 in which said weak bases are selected from the group consisting of ammonia, substituted and unsubstituted alkyl primary, secondary and tertiary amines, polyamines and alkanolamines, containing about 1 to 20 carbon atoms.

13. The method of claim 10 in which said chromatographic resin is of the ion exclusion type capable of chromatographically separating said weak cations by selective temporary retention but which passes strong cations in the column void volume.

14. The method of claim 10 in which the chromatographic resin is of a non-ionic type.

15. The method of claim 10 in which the chromatographic resin is an anion exchange resin with an ion exchange capacity between 10% and 100% of total theoretical capacity.

16. The method of claim 10 in which the chromatographic resin is an anion exchange resin in the hydroxide ion form.

17. The method of claim 16 in which said sample includes soluble anions which are removed by ion exchange with said chromatographic resin.

18. Apparatus for the chromatographic separation and quantitative analysis of a plurality of different weakly ionic species in weakly dissociated acids or bases or in salts of weakly dissociated acids or bases in a sample solution, all of said weak ionic species being of a positive or negative charge, said apparatus comprising
 (a) a chromatographic column including chromatographic resin in a form to substantially resolve weakly ionized ion species in a sample solution comprising a plurality of different weakly ionic species in weakly dissociated acids or bases or in salts of weakly dissociated acids or bases, but in a form to pass strongly ionized ionic species of the same charge in substantially unresolved form in the resin void volume,
 (b) means for supplying said sample and a strong acid or strong base of like charge to said sample ionic species,
 (c) stripper column means including ion exchange resin consisting essentially of identically charged ion exchange sites to said ionic species and adapted to remove the anion of said acid or cation of said base, but not to disturb the resolution of said weakly ionized ionic species from said chromatographic column,
 (d) a first conduit between said chromatographic column and said stripper column,
 (e) a conductivity cell and associated readout means, and
 (f) a second conduit between said stripper column and conductivity cell.

19. The apparatus of claim 18 in which said stripper column is in silver form.

20. The apparatus of claim 18 in which said chromatographic resin is in the hydrogen ion form.

21. The apparatus of claim 18 in which said ion exchange resin is in the sulfate form.

22. The apparatus of claim 18 in which the chromatographic resin is in the hydroxide form.

23. The apparatus of claim 18 in which the chromatographic resin is non-ionic.

24. The apparatus of claim 18 in which said chromatographic column comprises the only separation means for said ionic species.

25. The apparatus of claim 12 in which the chromatographic resin in said chromatographic column is characterized by an ion exchange capacity between 10% and 100% of total theoretical capacity.

* * * * *